US012245865B2

(12) United States Patent
Ostrand et al.

(10) Patent No.: US 12,245,865 B2
(45) Date of Patent: Mar. 11, 2025

(54) MONITORING AND QUERYING AUTOBIOGRAPHICAL EVENTS (71) Applicant: International Business Machines Corporation, Armonk, NY (US)

(72) Inventors: Rachel Ostrand, Milford, PA (US); Jenna Reinen, Rye Brook, NY (US); Ryan Anderson, Kensington, CA (US); Joseph Kozhaya, Morrisville, NC (US)

(73) Assignee: International Business Machines Corporation, Armonk, NY (US)

( * ) Notice: Subject to any disclaimer, the term of this patent is extended or adjusted under 35 U.S.C. 154(b) by 727 days.

(21) Appl. No.: 17/453,659

(22) Filed: Nov. 5, 2021

(65) Prior Publication Data
US 2023/0147846 A1 May 11, 2023

(51) Int. Cl.
*A61B 5/16* (2006.01)
*A61B 5/00* (2006.01)
(Continued)

(52) U.S. Cl.
CPC ............ *A61B 5/4088* (2013.01); *A61B 5/165* (2013.01); *A61B 5/4842* (2013.01); *G06F 40/20* (2020.01); *G16H 10/60* (2018.01); *G16H 15/00* (2018.01)

(58) Field of Classification Search
CPC ..... A61B 5/4088; A61B 5/4842; A61B 5/165; G06F 40/20; G16H 10/60; G16H 10/20; G16H 15/00; G16H 50/20; G16H 50/30
See application file for complete search history.

(56) References Cited

U.S. PATENT DOCUMENTS

| 5,321,396 A | 6/1994 | Lamming |
| 5,539,665 A | 7/1996 | Lamming |

(Continued)

FOREIGN PATENT DOCUMENTS

| CN | 101553855 A | 10/2009 |
| CN | 109478267 A | 3/2019 |

OTHER PUBLICATIONS

Authors et al. Disclosed Anonymously, "A method to generate a dynamic questionnaire out of the encoding of a prescriptive document", An IP.com Prior Art Database Technical Disclosure, IP.com No. IPCOM000257385D, IP.com Electronic Publication Date: Feb. 8, 2019, 9 Pages.

(Continued)

*Primary Examiner* — Ting Z Lee
(74) *Attorney, Agent, or Firm* — Joseph P. Curcuru (57) ABSTRACT

In an approach to monitoring and querying autobiographical events, one or more computer processors receive data from one or more sensors associated with a user. Based on the received data from the one or more sensors, one or more computer processors detect an autobiographical event associated with the user. One or more computer processors convert the received data from the one or more sensors into one or more observations associated with the autobiographical event. One or more computer processors convert the one or more observations into one or more questions associated with the one or more observations. One or more computer processors query the user with the one or more questions. One or more computer processors receive at least one response to the one or more questions from the user.

20 Claims, 3 Drawing Sheets

(51) Int. Cl.
  *G06F 40/20*  (2020.01)
  *G16H 10/60* (2018.01)
  *G16H 15/00* (2018.01)

(56) References Cited

U.S. PATENT DOCUMENTS

| | | | |
|---|---|---|---|
| 5,799,276 | A | 8/1998 | Komissarchik |
| 6,665,640 | B1 | 12/2003 | Bennett |
| 7,702,508 | B2 | 4/2010 | Bennett |
| 9,814,894 | B2* | 11/2017 | Kaib ............... A61B 5/48 |
| 9,967,211 | B2 | 5/2018 | Galley |
| 10,885,485 | B2 | 1/2021 | Brannon |
| 10,937,526 | B2 | 3/2021 | Cox |
| 11,033,216 | B2 | 6/2021 | Sbodio |
| 2007/0124292 | A1 | 5/2007 | Kirshenbaum |
| 2009/0083070 | A1* | 3/2009 | Giftakis ......... A61N 1/36132 705/2 |
| 2018/0325426 | A1* | 11/2018 | Shaw ............... G16H 40/67 |
| 2019/0205726 | A1 | 7/2019 | Khabiri |
| 2019/0359056 | A1* | 11/2019 | Wilson ............ G16H 50/30 |
| 2020/0143701 | A1* | 5/2020 | Letzt ............ A61B 5/4833 |
| 2020/0258609 | A1* | 8/2020 | McMaster ......... G16H 10/40 |
| 2021/0282722 | A1* | 9/2021 | Volpe ............ A61B 5/7475 |
| 2024/0062856 | A1* | 2/2024 | Haddad ......... A61B 5/02405 |

OTHER PUBLICATIONS

Authors et al. Disclosed Anonymously, "Dynamic Chatbot Engagement in Virtual Classrooms", An IP.com Prior Art Database Technical Disclosure, IP.com No. IPCOM000262638D, IP.com Electronic Publication Date: Jun. 17, 2020, 8 Pages.

Authors et al. Disclosed Anonymously, "Personalized multilingual chatbot at scale", An IP.com Prior Art Database Technical Disclosure, IP.com No. IPCOM000259381D, IP.com Electronic Publication Date: Aug. 7, 2019, 5 Pages.

Hitchcock et al., "Memory Category Fluency, Memory Specificity, and the Fading Affect Bias for Positive and Negative Autobiographical Events: Performance on a Good Day-Bad Day Task in Healthy and Depressed Individuals", Journal of Experimental Psychology: General, vol. 149, No. 1, 2020, 9 Pages.

Persons et al., "Developing and Using a Case Formulation to Guide Cognitive—Behavior Therapy", Journal of Psychology & Psychotherapy, 5:3, May 5, 2015, 9 Pages.

Stone, Arthur A., "Subjective Wellbeing Assessment for Survey Research", WHO Technical Meeting, Dec. 2012, 54 Pages.

"Patent Cooperation Treaty PCT International Search Report", Applicant's File Reference: PF220917PCT, International Application No. PCT/CN2022/129584, International Filing Date: Nov. 3, 2022, Date of Mailing: Jan. 28, 2023, 10 pages.

* cited by examiner

MONITORING AND QUERYING AUTOBIOGRAPHICAL EVENTS

BACKGROUND OF THE INVENTION

The present invention relates generally to the field of natural language processing, and more particularly to monitoring and querying autobiographical events.

Natural language processing (NLP) is a field of computer science, artificial intelligence, and linguistics concerned with the interactions between computers and human (natural) languages. As such, natural language processing is related to the area of human-computer interaction. Many challenges in natural language processing involve natural language understanding, that is, enabling computers to derive meaning from human or natural language input.

The Internet of Things (IoT) is the inter-networking of physical devices (also referred to as "connected devices" and "smart devices"), vehicles, buildings, and other items, embedded with electronics, software, sensors, actuators, and network connectivity that enable these objects to collect and exchange data. The IoT allows objects to be sensed and/or controlled remotely across existing network infrastructure, creating opportunities for more direct integration of the physical world into computer-based systems, and resulting in improved efficiency, accuracy, and economic benefit in addition to reduced human intervention. Each "thing" is uniquely identifiable through its embedded computing system but is able to interoperate within the existing Internet infrastructure.

Memory decline occurs as individuals age. Memory impairment is a significant issue for aging individuals who want to function independently; however, it may be difficult to acquire a personalized profile of changes in memory over time. Many cognitive memory tests assess factual memory as opposed to personal information; however, it may be more important to assess how the person is able to function, e.g., live independently, than whether the person remembers objective facts. Infrequent assessments by caregivers may not provide enough data for a complete or correct understanding of the state of the memory of an individual. Advances in biometric sensors enable tracking of an at-risk individual by family members and/or health care professionals. Similarly, advances in natural language processing (NLP) enable monitoring an individual from objective, external sources that may assess more complex cognitive function, such as speech and social interaction. Conversation-based digital assistants are gaining popularity; however, the ability to leverage information received by a digital assistant into an autobiographic schema for clinical assessment is underdeveloped. A digital assistant is limited in its ability to assess memory loss of a user because the digital assistant does not have an associated memory capability to store temporal information, such as user-specific facts, that can be queried at a later time.

SUMMARY

A first aspect of the present invention discloses a computer-implemented method including one or more computer processors receiving data from one or more sensors associated with a user. Based on the received data from the one or more sensors, one or more computer processors detect an autobiographical event associated with the user. One or more computer processors convert the received data from the one or more sensors into one or more observations associated with the autobiographical event. One or more computer processors convert the one or more observations into one or more questions associated with the one or more observations. One or more computer processors query the user with the one or more questions. One or more computer processors receive at least one response to the one or more questions from the user. The present invention has the advantage of providing a system that integrates a conversational agent to leverage casual, non-intrusive interactions with the individual based on data from a plurality of multimedia sensors and triggers and to query the individual regarding detected autobiographical events.

A second aspect of the present invention discloses a computer program product including one or more computer readable storage media and program instructions collectively stored on the one or more computer readable storage media. The stored program instructions include program instructions to receive data from one or more sensors associated with a user. The stored program instructions include program instructions to detect an autobiographical event associated with the user based on the received data from the one or more sensors. The stored program instructions include program instructions to convert the received data from the one or more sensors into one or more observations associated with the autobiographical event. The stored program instructions include program instructions to convert the one or more observations into one or more questions associated with the one or more observations. The stored program instructions include program instructions to query the user with the one or more questions. The stored program instructions include program instructions to receive at least one response to the one or more questions from the user.

A third aspect of the present invention discloses a computer system including one or more computer processors and one or more computer readable storage media, where program instructions are collectively stored on the one or more computer readable storage media. The stored program instructions include program instructions to receive data from one or more sensors associated with a user. The stored program instructions include program instructions to detect an autobiographical event associated with the user based on the received data from the one or more sensors. The stored program instructions include program instructions to convert the received data from the one or more sensors into one or more observations associated with the autobiographical event. The stored program instructions include program instructions to convert the one or more observations into one or more questions associated with the one or more observations. The stored program instructions include program instructions to query the user with the one or more questions. The stored program instructions include program instructions to receive at least one response to the one or more questions from the user.

In another aspect, the present invention discloses a method including one or more computer processors determining an accuracy of the at least one response to the one or more questions from the user. One or more computer processors determine the accuracy of the at least one response to the one or more questions from the user does not exceed a pre-defined accuracy threshold. One or more computer processors transmit an alert to one or more caregivers of the user. An advantage of alerting one or more caregivers of the response accuracy not exceeding the pre-defined threshold is that it may improve the well-being of an individual.

DETAILED DESCRIPTION

Embodiments of the present invention recognize that data collection for memory assessment of an individual may be improved by providing a system that integrates a conversational agent to leverage casual, non-intrusive interactions with the individual based on data from a plurality of multimedia sensors and triggers and to query the individual regarding detected autobiographical events. Embodiments of the present invention also recognize that the well-being of an individual may be improved by alerting a caregiver when a memory anomaly is detected. Implementation of embodiments of the invention may take a variety of forms, and exemplary implementation details are discussed subsequently with reference to the Figures.

Figure 1:
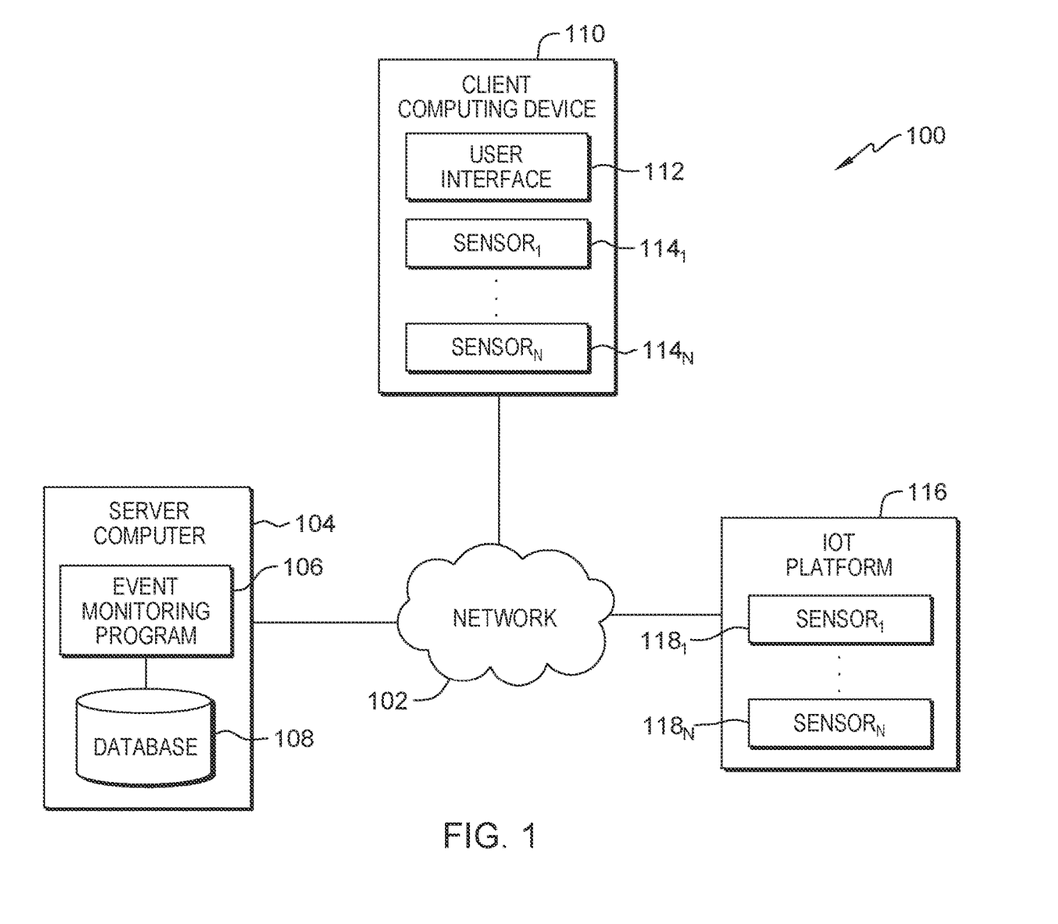
FIG. 1 is a functional block diagram illustrating a distributed data processing environment, in accordance with an embodiment of the present invention.

FIG. 1 is a functional block diagram illustrating a distributed data processing environment, generally designated 100, in accordance with one embodiment of the present invention. The term "distributed" as used herein describes a computer system that includes multiple, physically distinct devices that operate together as a single computer system. FIG. 1 provides only an illustration of one implementation and does not imply any limitations with regard to the environments in which different embodiments may be implemented. Many modifications to the depicted environment may be made by those skilled in the art without departing from the scope of the invention as recited by the claims.

Distributed data processing environment 100 includes server computer 104, client computing device 110, and Internet of Things (IoT) platform 116, all interconnected over network 102. Network 102 can be, for example, a telecommunications network, a local area network (LAN), a wide area network (WAN), such as the Internet, or a combination of the three, and can include wired, wireless, or fiber optic connections. Network 102 can include one or more wired and/or wireless networks capable of receiving and transmitting data, voice, and/or video signals, including multimedia signals that include voice, data, and video information. In general, network 102 can be any combination of connections and protocols that will support communications between server computer 104, client computing device 110, IoT platform 116, and other computing devices (not shown) within distributed data processing environment 100.

Server computer 104 can be a standalone computing device, a management server, a web server, a mobile computing device, or any other electronic device or computing system capable of receiving, sending, and processing data. In other embodiments, server computer 104 can represent a server computing system utilizing multiple computers as a server system, such as in a cloud computing environment. In another embodiment, server computer 104 can be a laptop computer, a tablet computer, a netbook computer, a personal computer (PC), a desktop computer, a personal digital assistant (PDA), a smart phone, an edge device, a containerized workload, or any programmable electronic device capable of communicating with client computing device 110, IoT platform 116, and other computing devices (not shown) within distributed data processing environment 100 via network 102. In another embodiment, server computer 104 represents a computing system utilizing clustered computers and components (e.g., database server computers, application server computers, etc.) that act as a single pool of seamless resources when accessed within distributed data processing environment 100. Server computer 104 includes event monitoring program 106 and database 108. Server computer 104 may include internal and external hardware components, as depicted and described in further detail with respect to FIG. 3.

Event monitoring program 106 collates data recordings of autobiographical events from a collection of sensors acting as observing agents and converts the data into natural language prompts and/or questions, the answers to which can be used to assess functionally relevant memory of the individual. Event monitoring program 106 receives sensor data. Based on the received sensor data, event monitoring program 106 detects an autobiographical event. Event monitoring program 106 converts the sensor data into observations and converts the observations into questions. Event monitoring program 106 stores the observations and associated questions. If event monitoring program 106 determines a pre-defined time threshold is not exceeded, then event monitoring program 106 continues to receive sensor data. If event monitoring program 106 determines a pre-defined time threshold is exceeded, then event monitoring program 106 queries the user with the stored questions. Event monitoring program 106 receives responses to the questions and determines the accuracy of the responses. If event monitoring program 106 determines a pre-defined accuracy threshold is not exceeded, then event monitoring program 106 transmits an alert to a caregiver. Event monitoring program 106 generates and transmits a report. Event monitoring program 106 stores the report. Event monitoring program 106 is depicted and described in further detail with respect to FIG. 2.

It should be noted herein that in the described embodiments, participating parties have consented to being recorded and monitored, and participating parties are aware of the potential that such recording and monitoring may be taking place. In various embodiments, for example, when downloading or operating an embodiment of the present invention, the embodiment of the invention presents a consent form and a terms and conditions prompt enabling the user to opt-in to participation. These embodiments may also include periodic reminders of such recording and monitoring throughout the course of any such use. Certain embodiments may also include regular (e.g., daily, weekly, monthly) reminders to the participating parties that they have consented to being recorded and monitored for memory assessment and may provide the participating parties with the opportunity to revoke consent of such recording and monitoring if desired. Furthermore, to the extent that any non-participating parties' actions are recorded (for example, when a package is delivered), such monitoring takes place for the limited purpose of providing support to the detection of an autobiographical event, with protections in place to prevent the unauthorized use or disclosure of any data for which an individual might have a certain expectation of privacy. For example, if a sensor collects an image of an individual's face, a technique such as facial blurring is utilized to protect the identity of the individual.

Database 108 stores information used by and generated by event monitoring program 106, client computing device 110, and IoT platform 116. In the depicted embodiment, database 108 resides on server computer 104. In another embodiment, database 108 may reside elsewhere within distributed data processing environment 100, provided that event monitoring program 106, client computing device 110, and IoT platform 116 have access to database 108, via network 102. A database is an organized collection of data. Database 108 can be implemented with any type of storage device capable of storing data and configuration files that can be accessed and utilized by event monitoring program 106 and IoT platform 116, such as a database server, a hard disk drive, or a flash memory. Database 108 stores data from a plurality of sensors that reside on client computing device 110 and IoT platform 116. In an embodiment, the data received from the plurality of sensors and/or IoT platform 116 is stored as encrypted data. Database 108 may also store historical statistics of the sensor data, such as averages, for future comparison. Database 108 also stores observations made by event monitoring program 106 based on the sensor data as well as questions generated by event monitoring program 106 based on the observations. Further, database 108 stores one or more reports generated by event monitoring program 106. Database 108 may also store a distribution list of caregivers for transmission of the reports and/or alerts.

In addition, database 108 stores a user profile for the user of client computing device 110. The user profile may include, but is not limited to, the name of the user, one or more alternate names of the user, a voice sample, a checklist of medical conditions, etc. In addition, the user profile may include identification and/or demographic information associated with one or more common visitors and/or conversational partners. In an embodiment, a small number of close associates and/or common visitors of the user are registered with event monitoring program 106, through their voice recordings and some biographical information, e.g., a name, a relationship to the user (e.g., a role and/or a title such as "sister"), a voice sample, etc., creating a speaker profile for future identification of the visitor. In an embodiment, prior to storing any data associated with a common visitor and/or conversational partner, event monitoring program 106 requests and receives consent from the common visitor and/or conversational partner to use the personal information included in the speaker profile. The user profile may also include user preferences. For example, a user may define preferred locations, such as stores, parks, etc., that the user commonly visits such that event monitoring program 106 can detect changes to the user's routine. In another example, the user may specify which information can be included in an alert and/or a report generated by event monitoring program 106.

The present invention may contain various accessible data sources, such as database 108, that may include personal data, content, or information the user wishes not to be processed. Personal data includes personally identifying information or sensitive personal information as well as user information, such as tracking or geolocation information. Processing refers to any operation, automated or unautomated, or set of operations such as collecting, recording, organizing, structuring, storing, adapting, altering, retrieving, consulting, using, disclosing by transmission, dissemination, or otherwise making available, combining, restricting, erasing, or destroying personal data. Event monitoring program 106 enables the authorized and secure processing of personal data. Event monitoring program 106 provides informed consent, with notice of the collection of personal data, allowing the user to opt in to processing personal data. Consent can take several forms. Opt-in consent can impose on the user to take an affirmative action before personal data is processed. Event monitoring program 106 provides information regarding personal data and the nature (e.g., type, scope, purpose, duration, etc.) of the processing. Event monitoring program 106 provides the user with copies of stored personal data. Event monitoring program 106 allows the correction or completion of incorrect or incomplete personal data. Event monitoring program 106 allows the immediate deletion of personal data.

Client computing device 110 can be one or more of a laptop computer, a tablet computer, a smart phone, smart watch, a smart speaker, or any programmable electronic device capable of communicating with various components and devices within distributed data processing environment 100, via network 102. Client computing device 110 may be a wearable computer. Wearable computers are miniature electronic devices that may be worn by the bearer under, with, or on top of clothing, as well as in or connected to glasses, hats, or other accessories. Wearable computers are especially useful for applications that require more complex computational support than merely hardware coded logics. In an embodiment, the wearable computer may be in the form of a smart watch. In an embodiment, client computing device 110 may be integrated into a vehicle of the user. For example, client computing device 110 may include a heads-up display in the windshield of the vehicle. In general, client computing device 110 represents one or more programmable electronic devices or combination of programmable electronic devices capable of executing machine readable program instructions and communicating with other computing devices (not shown) within distributed data processing environment 100 via a network, such as network 102. Client computing device 110 includes an instance of user interface 112 and sensor $114_{1-N}$.

User interface 112 provides an interface between event monitoring program 106 on server computer 104 and a user of client computing device 110. In one embodiment, user interface 112 is mobile application software. Mobile application software, or an "app," is a computer program designed to run on smart phones, tablet computers and other mobile devices. In one embodiment, user interface 112 may be a graphical user interface (GUI) or a web user interface (WUI) and can display text, documents, web browser windows, user options, application interfaces, and instructions for operation, and include the information (such as graphic, text, and sound) that a program presents to a user and the control sequences the user employs to control the program. In an embodiment where client computing device 110 is associated with an individual whose memory is being monitored, user interface 112 enables the user of client computing device 110 to input user profile and preference information for use by event monitoring program 106, to be stored in database 108. In an embodiment where the user of client computing device 110 is a caregiver, user interface 112 enables the user to receive alerts and reports from event monitoring program 106. As used herein, the term caregiver can include a family member, a healthcare professional, such as a doctor, a nurse, a psychologist, a clinician, etc., or any person with an interest in monitoring the state of the user's memory, with appropriate consent from the user.

IoT platform 116 is a suite of components that enable a) deployment of applications that monitor, manage, and control connected devices and sensors; b) remote data collection from connected devices; and c) independent and secure connectivity between devices. The suite of components may include, but are not limited to, a hardware architecture, an operating system, a runtime library, an edge device, and/or a containerized workload (not shown). In the depicted embodiment, IoT platform 116 includes sensor $118_{1-N}$. In another embodiment, IoT platform 116 may include a plurality of other computing devices.

A sensor is a device that detects or measures a physical property and then records or otherwise responds to that property, such as vibration, chemicals, radio frequencies, environment, weather, humidity, light, etc. Sensor $114_{1-N}$ and sensor $118_{1-N}$, herein sensor(s) 114 and sensor(s) 118, detect a plurality of attributes of client computing device 110 and IoT platform 116, respectively. As used herein, N represents a positive integer, and accordingly the number of scenarios implemented in a given embodiment of the present invention is not limited to those depicted in FIG. 1. Sensor(s) 114 and sensor(s) 118 may be one or more of a plurality of types of camera, including, but not limited to, pin-hole, stereo, omni-directional, non-central, infrared, video, digital, three dimensional, panoramic, filter-based, wide-field, narrow-field, telescopic, microscopic, etc. In some embodiments, sensor(s) 114 and sensor(s) 118 include any device capable of imaging a portion of the electromagnetic spectrum. Sensor(s) 114 and sensor(s) 118 may be one or more of a plurality of types of microphone for detecting speech and other audible sounds. Sensor(s) 114 and sensor(s) 118 may be able to detect weather conditions, such as air temperature, relative humidity, presence and type of precipitation, wind speed, etc. Sensor(s) 114 and sensor(s) 118 may be GPS sensors. For example, sensor(s) 114 may use GPS to detect the location of the user of client computing device 110. Sensor(s) 114 and sensor(s) 118 may include various types of pressure sensors and/or strain gauges to detect a person sitting or standing in a particular location. Sensor(s) 114 and sensor(s) 118 may include various types of accelerometers to detect movement or vibration of client computing device 110 and/or a component included in IoT platform 116. Sensor(s) 114 may include biometric sensors for detecting the physical condition of the user, such as blood pressure, heart rate, respiratory rate, calories burned, calories consumed, pulse, oxygen levels, blood oxygen level, glucose level, blood pH level, salinity of user perspiration, skin temperature, galvanic skin response, electrocardiography (ECG or EKG) data, body temperature, eye tracking data, etc. In one embodiment, sensor(s) 114 and sensor(s) 118 transmit data directly to database 108.

Figure 2:
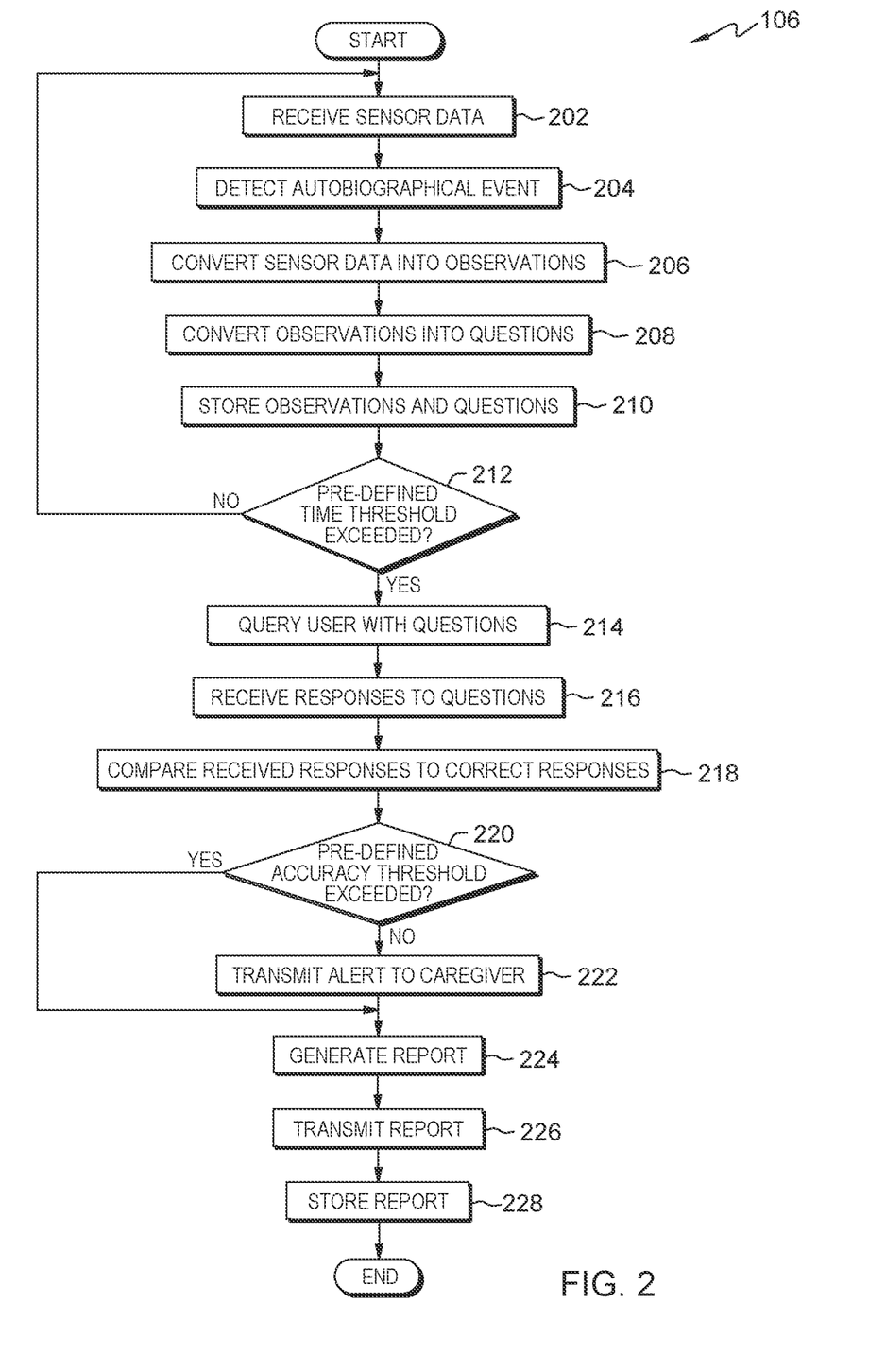
FIG. 2 is a flowchart depicting operational steps of an event monitoring program, on a server computer within the distributed data processing environment of FIG. 1, for monitoring and querying autobiographical events, in accordance with an embodiment of the present invention.

FIG. 2 is a flowchart depicting operational steps of event monitoring program 106, on server computer 104 within distributed data processing environment 100 of FIG. 1, for monitoring and querying autobiographical events, in accordance with an embodiment of the present invention.

Event monitoring program 106 receives sensor data (step 202). In an embodiment, as sensor(s) 114 and/or sensor(s) 118 continuously generate data, event monitoring program 106 receives the data. In an embodiment where sensor(s) 114 and/or sensor(s) 118 transmit data directly to database 108, event monitoring program 106 retrieves the sensor data from database 108. Sensor(s) 114 and sensor(s) 118 act as observing agents deployed in the environment of the user. The sensor data may include, but is not limited to, audio recordings in the user's home, e.g., the user speaking on the phone or a visitor's voice, video recordings in the user's home, e.g., the user moving from one room to another room, location data associated with the user, e.g., GPS data associated with client computing device 110, data indicating the use of smart appliances included in IoT platform 116, e.g., a refrigerator door opening, use of a stove, etc., biometric readings, e.g., heart rate of the user, etc. In an embodiment, the received sensor data is metadata that does not include identifying numbers. For example, GPS data includes a geographic location but does not include a home and/or name label.

Event monitoring program 106 detects an autobiographical event (step 204). In an embodiment, event monitoring program 106 analyzes the received sensor data and determines whether the data indicates an event associated with the user, i.e., an autobiographical event, has occurred. Event monitoring program 106 uses the sensor data to track events and social interactions that occur in the day-to-day life of the user. For example, event monitoring program 106 detects the voice of a person, via a microphone included in sensor(s) 118, that does not match the voice of the user. In another example, event monitoring program 106 detects a location change of the user, via a GPS sensor included in sensor(s) 114. Other examples of autobiographical events include, but are not limited to, a family visit day, eating, speaking, moving, sleeping, and external events, such as receiving a delivered package.

Event monitoring program 106 converts the sensor data into observations (step 206). In an embodiment, event monitoring program 106 uses one or more NLP and/or artificial intelligence (AI) techniques to extract factual, autobiographical information from the sensor data about events in the user's day-to-day life, called observations, which is an advantage over systems that test cognitive memory using only factual information. In an embodiment, observations are statements describing the autobiographical event. Continuing the first previous example, based on detecting a voice that does not match the voice of the user, event monitoring program 106 determines that the user has a visitor. In an embodiment, event monitoring program 106 also uses one or more NLP techniques to extract the context of the conversation, i.e., determining whether the user is a friend or a handyman. Continuing the second previous example, based on the detected location change of the user, event monitoring program 106 determines that the user moved from the home to a nearby store, and, because of the speed at which the user arrived at the store, event monitoring program 106 determines the user walked to the store. In an embodiment, event monitoring program 106 also determines a timestamp of the event.

In an embodiment, event monitoring program 106 determines whether the extracted observations are associated with an event that event monitoring program 106 classifies as atypical and/or an outlier, as compared with historical autobiographical events stored in database 108. In the embodiment, event monitoring program 106 performs simple statistics to produce counts of categories of events, for example, social or physical, to generate a distribution. Event monitoring program 106 compares a single event to the distribution to determine whether or not the event is common, and, if so, to determine a level of commonality. For example, event monitoring program 106 may determine a change to the user's routine, such as a high or low rate of step count at odd hours, tagged social interactions at atypical times, lack of social interaction over a period of time, leaving the home at an atypical time, etc. In an embodiment, if event monitoring program 106 determines an event is atypical, an outlier, or more generally, memorable, then event monitoring program 106 flags the event. For example, sensor(s) 118 detect a delivery of a package in a blue box, and event monitoring program 106 flags the delivery as an event. In an embodiment, event monitoring program 106 protects privacy aspects of an interaction in an observation. Continuing the previous example, event monitoring program 106 converts the delivery of the blue box as an observation, but ignores the details of the delivery person, i.e., event monitoring program 106 does not track or save personal information associated with the delivery person, such as voice or video recordings.

Event monitoring program 106 converts the observations into questions (step 208). In an embodiment, event monitoring program 106 uses one or more NLP and/or AI techniques to convert the previously determined observations into a set of active questions about the autobiographical event. Continuing the first previous example, event monitoring program 106 converts the observation of a visitor in the user's home to a question, such as "Who was the friend that visited you on Monday?" or "What issue did the handyman fix for you?" Continuing the second previous example, event monitoring program 106 converts the observation of the user walking to the store to a question, such as "What did you buy at the hardware store last week?" or "Did you walk, drive or take public transportation to the hardware store last week?"

Event monitoring program 106 stores the observations and associated questions (step 210). In an embodiment, event monitoring program 106 stores the observations and the questions associated with the observations in database 108. In general, event monitoring program 106, in conjunction with sensor(s) 114 and sensor(s) 118, acts as a sensemaking system, where sensor(s) 114 and sensor(s) 118 are the observing agents. The advantage of a sensemaking system is that it can create situational awareness with properties such as identity and identification, retrospection, dialogues and narratives, and ongoing and continuous evaluation.

Event monitoring program 106 determines whether a pre-defined time threshold is exceeded (decision block 212). In an embodiment, event monitoring program 106 generates questions associated with autobiographical events such that event monitoring program 106 can query the user about the events at a pre-defined later time to generate data associated with the state of the user's memory. In an embodiment, the individual whose memory will be assessed determines the pre-defined time threshold and stores the pre-defined time threshold in database 108, via user interface 112. In another embodiment, a caregiver determines a frequency for testing the user's memory and stores the pre-defined time threshold in database 108. For example, the pre-defined time threshold may be a day, a week, or a month following the occurrence of an autobiographical event.

If event monitoring program 106 determines a pre-defined time threshold is not exceeded ("no" branch, decision block 212), then event monitoring program 106 returns to step 202 and continues to receive sensor data.

If event monitoring program 106 determines a pre-defined time threshold is exceeded ("yes" branch, decision block 212), then event monitoring program 106 queries the user with the questions (step 214). In an embodiment, event monitoring program 106 retrieves one or more questions stored in database 108, as discussed with respect to step 210, and interacts with the user conversationally about one or more autobiographical events that occurred prior to the pre-defined time threshold being exceeded, in order to dialog and measure functionally relevant memory. In an embodiment where event monitoring program 106 includes a conversational agent (not shown), event monitoring program 106 uses the conversational agent to query the user, via user interface 112. For example, event monitoring program 106 may ask the user "Who was the friend that visited you on Monday?" in a natural language speaking voice from a speaker associated with client computing device 110. An advantage of integrating a conversational agent is to leverage casual, non-intrusive interactions with the user based on sensor data regarding detected autobiographical events. In another example, event monitoring program 106 may send a text message to the user, via user interface 112, that displays the question.

Event monitoring program 106 receives responses to the questions (step 216). In an embodiment, event monitoring program 106 receives, via user interface 112, a response from the user to one or more of the questions posed to the user in the query. For example, if event monitoring program 106 posed the question "Who was the friend that visited you on Monday?" then the response from the user may be "It was Mary" or the response may be "I can't remember." In an embodiment, event monitoring program 106, using automatic speech recognition software, converts the user's speech to text and stores the textual responses in database 108.

Event monitoring program 106 compares the received responses to correct responses (step 218). In an embodiment, event monitoring program 106 compares the one or more received responses to the observation stored in association with the query in database 108 to determine whether the received responses are accurate and/or correct, i.e., match the stored observation. Responses that do not match the stored observation may indicate a memory anomaly, i.e., a change or decrease in memory function.

Event monitoring program 106 determines whether a pre-defined accuracy threshold is exceeded (decision block 220). The pre-defined accuracy threshold represents a quantity of correct responses to a defined number of questions over a defined period of time. In an embodiment, a caregiver pre-defines an accuracy threshold for responses to queries and stores the accuracy threshold in database 108. For example, the accuracy threshold may be defined as a percentage of questions answered correctly in one sitting, such as 75 percent. In another example, the accuracy threshold may be defined as a number of matching details in a response to a single question, such as in a response to the question "What are four things you bought at the store last week?" In an embodiment, the caregiver can adjust the accuracy threshold higher or lower as needed to better assess any changes in the memory of the user. The accuracy threshold is defined to indicate whether the user is experiencing a memory issue that may require a full evaluation and/or assessment by a doctor and/or another clinician.

If event monitoring program 106 determines the accuracy threshold is not exceeded ("no" branch, decision block 220), then event monitoring program 106 transmits an alert to a caregiver (step 222). In an embodiment, if the accuracy of the user's response to the one or more questions does not exceed the pre-defined accuracy threshold, indicating a potentially serious issue with the memory status of the user, then event monitoring program 106 transmits an alert to one or more caregivers, such as a family member and/or a clinician. For example, event monitoring program 106 may transmit an email or text message to the caregiver that indicates the user's responses to a series of queries was below the pre-defined accuracy threshold and that a clinical evaluation should be considered.

Responsive to transmitting an alert, or if event monitoring program 106 determines the accuracy threshold is exceeded ("yes" branch, decision block 220), then event monitoring program 106 generates a report (step 224). In an embodiment, event monitoring program 106 generates a report including the one or more of the received sensor data, the observations, the questions, and the responses to the questions. In an embodiment, event monitoring program 106 includes any determined indications of observations that are associated with an event that event monitoring program 106 classifies as atypical and/or an outlier in the report. In an embodiment, event monitoring program 106 includes in the report a notation of whether or not the responses exceeded the pre-defined accuracy threshold and, if not, then details of the transmitted alert. In an embodiment, event monitoring program 106 generates a report when the pre-defined time threshold is exceeded. In another embodiment, event monitoring program 106 generates a report at a pre-defined frequency. For example, event monitoring program 106 may generate a monthly report. In yet another embodiment, event monitoring program 106 generates a report after an accumulation of a pre-defined number of observations. For example, event monitoring program 106 may generate a report after the user leaves and returns to the home ten times. In an embodiment, event monitoring program 106 generates data associated with long term trends in the user's memory accuracy based on historical data stored in database 108 and includes the trend data in the report.

Event monitoring program 106 transmits the report (step 226). In an embodiment, in response to generating the report, event monitoring program 106 transmits the report to one or more caregivers, such as a family member and/or a clinician. For example, event monitoring program 106 may transmit an email or text message to the caregiver that includes the report. In an embodiment, a report distribution list is stored in database 108, and event monitoring program 106 transmits the report to the distribution list. The one or more caregivers that receive the report may use the reported data and alerts to augment care for the user.

Event monitoring program 106 stores the report (step 228). In an embodiment, event monitoring program 106 stores the generated report in database 108. In an embodiment, instead of transmitting the report, event monitoring program 106 transmits a link to the report in database 108 in an email or text message to a caregiver, and the caregiver can retrieve the report via the link.

The following are several examples of use cases for event monitoring program 106.

A user's sister, Mary, visits the user on Tuesday. Sensor(s) 118 include a microphone that picks up two voices. Event monitoring program 106 uses one or more of noise-cancelling technology, speaker diarization, and automatic speech recognition techniques to determine there are two speakers and matches the voices to voice samples in database 108 of the user and Mary and identifies her as the user's sister. Event monitoring program 106 converts the sensor data into the observation of a visit from Mary on Tuesday, as discussed with respect to step 206. Event monitoring program 106 converts the observation into questions, as discussed with respect to step 208, such as "Who visited you last week?" and "What are some topics that you discussed with Mary when she visited you?" and stores the questions in association with the observation in database 108, as discussed with respect to step 210. After the pre-defined time threshold is exceeded, event monitoring program 106 queries the user with the stored questions, as discussed with respect to step 214.

A user orders takeout food from a restaurant on Wednesday. Sensor(s) 114 include a monitor of charges to the user's credit card that detects the transaction with the restaurant. Sensor(s) 118 include a camera that detects the user bringing the food into the kitchen. Event monitoring program 106 uses one or more visual recognition techniques to determine the takeout food is pizza and uses the charge alert from the credit card to determine the restaurant from which the food was ordered. Event monitoring program 106 converts the sensor data into the observation of a takeout pizza, as discussed with respect to step 206. Event monitoring program 106 converts the observation into questions, as discussed with respect to step 208, such as "What restaurant did you order takeout from last Wednesday?" and "What type of food did you have delivered?" and stores the questions in association with the observation in database 108, as discussed with respect to step 210. After the pre-defined time threshold is exceeded, event monitoring program 106 queries the user with the stored questions, as discussed with respect to step 214.

A user cooks a pot roast for dinner on Thursday. Sensor(s) 118 include a smart refrigerator that detects when the door is opened and closed and what ingredients are removed, as well as a smart oven that detects when and for how long the oven is on. Event monitoring program 106 converts the sensor data into the observation of the user cooking the pot roast on Thursday, as discussed with respect to step 206. Event monitoring program 106 converts the observation into questions, as discussed with respect to step 208, such as "What meal did you cook for dinner on Thursday?" and stores the questions in association with the observation in database 108, as discussed with respect to step 210. After the pre-defined time threshold is exceeded, event monitoring program 106 queries the user with the stored questions, as discussed with respect to step 214.

A user takes a long walk to the park on Sunday. Client computing device 110 is a smart watch. Sensor(s) 114 include an accelerometer that detects the number of steps the user takes and GPS that detects the location to which the user traveled. Sensor(s) 114 can also detect weather conditions, such as air temperature, relative humidity, presence and type of precipitation, wind speed, etc. Event monitoring program 106 converts the sensor data into the observation of a long walk to the park on Sunday in the rain, as discussed with respect to step 206. In addition, event monitoring program 106 compares the number of steps taken by the user to the historical average, stored in database 108, to determine whether the number of steps deviated significantly from the average. Event monitoring program 106 converts the observation into questions, as discussed with respect to step 208, such as "Where did you walk to on Sunday?" and stores the questions in association with the observation in database 108, as discussed with respect to step 210. After the pre-defined time threshold is exceeded, event monitoring program 106 queries the user with the stored questions, as discussed with respect to step 214.

Figure 3:
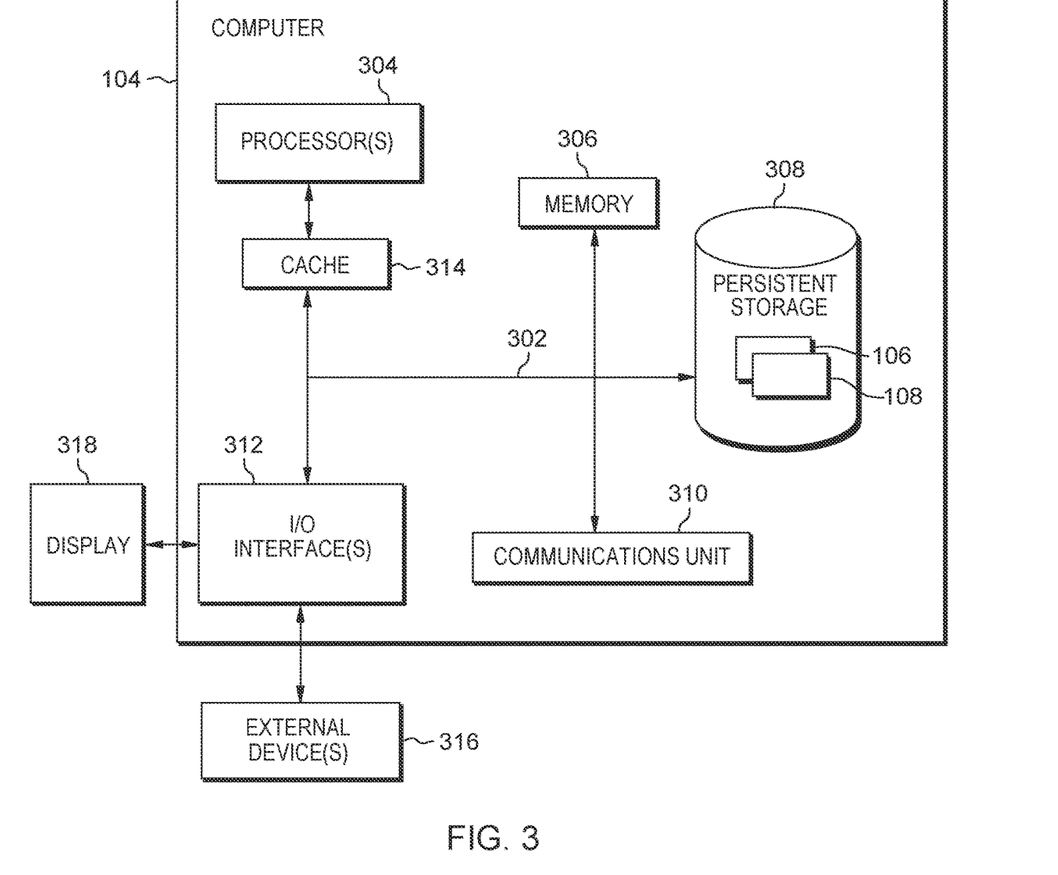
FIG. 3 depicts a block diagram of components of the server computer executing the event monitoring program within the distributed data processing environment of FIG. 1, in accordance with an embodiment of the present invention.

FIG. 3 depicts a block diagram of components of server computer 104 within distributed data processing environment 100 of FIG. 1, in accordance with an embodiment of the present invention. It should be appreciated that FIG. 3 provides only an illustration of one implementation and does not imply any limitations with regard to the environments in which different embodiments can be implemented. Many modifications to the depicted environment can be made.

Server computer 104 can include processor(s) 304, cache 314, memory 306, persistent storage 308, communications unit 310, input/output (I/O) interface(s) 312 and communications fabric 302. Communications fabric 302 provides communications between cache 314, memory 306, persistent storage 308, communications unit 310, and input/output (I/O) interface(s) 312. Communications fabric 302 can be implemented with any architecture designed for passing data and/or control information between processors (such as microprocessors, communications and network processors, etc.), system memory, peripheral devices, and any other hardware components within a system. For example, communications fabric 302 can be implemented with one or more buses.

Memory 306 and persistent storage 308 are computer readable storage media. In this embodiment, memory 306 includes random access memory (RAM). In general, memory 306 can include any suitable volatile or non-volatile computer readable storage media. Cache 314 is a fast memory that enhances the performance of processor(s) 304 by holding recently accessed data, and data near recently accessed data, from memory 306.

Program instructions and data used to practice embodiments of the present invention, e.g., event monitoring program 106 and database 108, are stored in persistent storage 308 for execution and/or access by one or more of the respective processor(s) 304 of server computer 104 via cache 314. In this embodiment, persistent storage 308 includes a magnetic hard disk drive. Alternatively, or in addition to a magnetic hard disk drive, persistent storage 308 can include a solid-state hard drive, a semiconductor storage device, a read-only memory (ROM), an erasable programmable read-only memory (EPROM), a flash memory, or any other computer readable storage media that is capable of storing program instructions or digital information.

The media used by persistent storage 308 may also be removable. For example, a removable hard drive may be used for persistent storage 308. Other examples include optical and magnetic disks, thumb drives, and smart cards that are inserted into a drive for transfer onto another computer readable storage medium that is also part of persistent storage 308.

Communications unit 310, in these examples, provides for communications with other data processing systems or devices, including resources of client computing device 110 and IoT platform 116. In these examples, communications unit 310 includes one or more network interface cards. Communications unit 310 may provide communications through the use of either or both physical and wireless communications links. Event monitoring program 106, database 108, and other programs and data used for implementation of the present invention, may be downloaded to persistent storage 308 of server computer 104 through communications unit 310.

I/O interface(s) 312 allows for input and output of data with other devices that may be connected to server computer 104. For example, I/O interface(s) 312 may provide a connection to external device(s) 316 such as a keyboard, a keypad, a touch screen, a microphone, a digital camera, and/or some other suitable input device. External device(s) 316 can also include portable computer readable storage media such as, for example, thumb drives, portable optical or magnetic disks, and memory cards. Software and data used to practice embodiments of the present invention, e.g., event monitoring program 106 and database 108 on server computer 104, can be stored on such portable computer readable storage media and can be loaded onto persistent storage 308 via I/O interface(s) 312. I/O interface(s) 312 also connect to a display 318.

Display 318 provides a mechanism to display data to a user and may be, for example, a computer monitor. Display 318 can also function as a touch screen, such as a display of a tablet computer.

The programs described herein are identified based upon the application for which they are implemented in a specific embodiment of the invention. However, it should be appreciated that any particular program nomenclature herein is used merely for convenience, and thus the invention should not be limited to use solely in any specific application identified and/or implied by such nomenclature.

The present invention may be a system, a method, and/or a computer program product. The computer program product may include a computer readable storage medium (or media) having computer readable program instructions thereon for causing a processor to carry out aspects of the present invention.

The computer readable storage medium can be any tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, a special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, a segment, or a portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The foregoing descriptions of the various embodiments of the present invention have been presented for purposes of illustration and example, but are not intended to be exhaustive or limited to the embodiments disclosed. Many modifications and variations will be apparent to those of ordinary skill in the art without departing from the scope and spirit of the invention. The terminology used herein was chosen to best explain the principles of the embodiment, the practical application or technical improvement over technologies found in the marketplace, or to enable others of ordinary skill in the art to understand the embodiments disclosed herein.

What is claimed is:

1. A computer-implemented method comprising:
    receiving, by one or more computer processors, data from one or more sensors associated with a user;
    based on the received data from the one or more sensors, detecting, by one or more computer processors, an autobiographical event associated with the user;
    converting, by one or more computer processors, the received data from the one or more sensors into one or more observations associated with the autobiographical event, wherein the one or more observations are statements describing the autobiographical event, wherein converting the received data into the one or more observations comprises:
        utilizing natural language processing (NLP) and artificial intelligence (AI) techniques to extract contextual information from the sensor data;
    converting, by one or more computer processors, the one or more observations into one or more questions associated with the one or more observations and the contextual information;
    utilizing a conversational agent to query, by one or more computer processors, the user through a user interface, with the one or more questions;
    receiving, by one or more computer processors, through the user interface at least one response to the one or more questions from the user; and
    comparing the at least one response to the one or more observations associated with the at least one query to determine that the received at least one response matches one or more stored observations.

2. The computer-implemented method of claim 1, further comprising:
    prior to querying the user with the one or more questions, determining, by one or more computer processors, a pre-defined time threshold is exceeded.

3. The computer-implemented method of claim 2, wherein the pre-defined time threshold is a defined period of time after the autobiographical event.

4. The computer-implemented method of claim 1, further comprising:
    storing, by one or more computer processors, the one or more observations and the one or more questions associated with the one or more observations.

5. The computer-implemented method of claim 1, further comprising:
    determining, by one or more computer processors, an accuracy of the at least one response to the one or more questions from the user;
    determining, by one or more computer processors, the accuracy of the at least one response to the one or more questions from the user does not exceed a pre-defined accuracy threshold; and
    transmitting, by one or more computer processors, an alert to one or more caregivers of the user.

6. The computer-implemented method of claim 5, wherein the pre-defined accuracy threshold is selected from the group consisting of a percentage of the one or more questions answered correctly by the user in one sitting and a number of matching details in a response to one question of the one or more questions.

7. The computer-implemented method of claim 1, further comprising:
generating, by one or more computer processors, a report based on one or more of the received data from the one or more sensors, the one or more observations, the one or more questions, and the at least one response to the one or more questions;
transmitting, by one or more computer processors, the report to one or more caregivers of the user; and
storing, by one or more computer processors, the report.

8. The computer-implemented method of claim 1, wherein detecting the autobiographical event associated with the user based on the received data from the one or more sensors includes using one or more natural language processing techniques.

9. A computer program product comprising:
one or more computer readable storage media and program instructions collectively stored on the one or more computer readable storage media, the stored program instructions comprising:
program instructions to receive, by one or more computer processors, data from one or more sensors associated with a user;
based on the received data from the one or more sensors, program instructions to detect, by one or more computer processors, an autobiographical event associated with the user;
program instructions to convert, by one or more computer processors, the received data from the one or more sensors into one or more observations associated with the autobiographical event, wherein the one or more observations are statements describing the autobiographical event, wherein converting the received data into the one or more observations comprises:
program instructions to utilize natural language processing (NLP) and artificial intelligence (AI) techniques to extract contextual information from the sensor data;
program instructions to convert, by one or more computer processors, the one or more observations into one or more questions associated with the one or more observations and the contextual information;
program instructions to utilize a conversational agent to query, by one or more computer processors, the user through a user interface, with the one or more questions;
program instructions to receive, by one or more computer processors, through the user interface at least one response to the one or more questions from the user; and
program instructions to compare the at least one response to the one or more observations associated with the at least one query to determine that the received at least one response matches one or more stored observations.

10. The computer program product of claim 9, the stored program instructions further comprising:
prior to querying the user with the one or more questions, program instructions to determine a pre-defined time threshold is exceeded.

11. The computer program product of claim 10, wherein the pre-defined time threshold is a defined period of time after the autobiographical event.

12. The computer program product of claim 9, the stored program instructions further comprising:
program instructions to determine an accuracy of the at least one response to the one or more questions from the user;
program instructions to determine the accuracy of the at least one response to the one or more questions from the user does not exceed a pre-defined accuracy threshold; and
program instructions to transmit an alert to one or more caregivers of the user.

13. The computer program product of claim 12, wherein the pre-defined accuracy threshold is selected from the group consisting of a percentage of the one or more questions answered correctly by the user in one sitting and a number of matching details in a response to one question of the one or more questions.

14. The computer program product of claim 9, the stored program instructions further comprising:
program instructions to generate a report based on one or more of the received data from the one or more sensors, the one or more observations, the one or more questions, and the at least one response to the one or more questions;
program instructions to transmit the report to one or more caregivers of the user; and
program instructions to store the report.

15. A computer system comprising:
one or more computer processors;
one or more computer readable storage media;
program instructions collectively stored on the one or more computer readable storage media for execution by at least one of the one or more computer processors, the stored program instructions comprising:
program instructions to receive, by one or more computer processors, data from one or more sensors associated with a user;
based on the received data from the one or more sensors, program instructions to detect, by one or more computer processors, an autobiographical event associated with the user;
program instructions to convert, by one or more computer processors, the received data from the one or more sensors into one or more observations associated with the autobiographical event, wherein the one or more observations are statements describing the autobiographical event, wherein converting the received data into the one or more observations comprises:
program instructions to utilize natural language processing (NLP) and artificial intelligence (AI) techniques to extract contextual information from the sensor data;
program instructions to convert, by one or more computer processors, the one or more observations into one or more questions associated with the one or more observations and the contextual information;
program instructions to utilize a conversational agent to query, by one or more computer processors, the user through a user interface, with the one or more questions;
program instructions to receive, by one or more computer processors, through the user interface at least one response to the one or more questions from the user; and
program instructions to compare the at least one response to the one or more observations associated with the at least one query to determine that the received at least one response matches one or more stored observations.

16. The computer system of claim 15, the stored program instructions further comprising:

prior to querying the user with the one or more questions, program instructions to determine a pre-defined time threshold is exceeded.

17. The computer system of claim 16, wherein the pre-defined time threshold is a defined period of time after the autobiographical event.

18. The computer system of claim 15, the stored program instructions further comprising:

program instructions to determine an accuracy of the at least one response to the one or more questions from the user;

program instructions to determine the accuracy of the at least one response to the one or more questions from the user does not exceed a pre-defined accuracy threshold; and program instructions to transmit an alert to one or more caregivers of the user.

19. The computer system of claim 18, wherein the pre-defined accuracy threshold is selected from the group consisting of a percentage of the one or more questions answered correctly by the user in one sitting and a number of matching details in a response to one question of the one or more questions.

20. The computer system of claim 15, the stored program instructions further comprising:

program instructions to generate a report based on one or more of the received data from the one or more sensors, the one or more observations, the one or more questions, and the at least one response to the one or more questions;

program instructions to transmit the report to one or more caregivers of the user; and program instructions to store the report.

* * * * *